US009037253B2

(12) United States Patent
Dhanasingh et al.

(10) Patent No.: US 9,037,253 B2
(45) Date of Patent: May 19, 2015

(54) SYSTEM AND METHOD FOR ELECTRODE SELECTION AND FREQUENCY MAPPING

(71) Applicant: MED-EL Elektromedizinische Geraete GmbH, Innsbruck (AT)

(72) Inventors: Anandhan Dhanasingh, Innsbruck (AT); Claude Jolly, Innsbruck (AT); Stefan B. Nielsen, Innsbruck (AT); Roland Hessler, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/179,885

(22) Filed: Feb. 13, 2014

(65) Prior Publication Data

US 2014/0228909 A1 Aug. 14, 2014

Related U.S. Application Data

(60) Provisional application No. 61/764,778, filed on Feb. 14, 2013.

(51) Int. Cl.

| | |
|---|---|
| ***A61N 1/00*** | (2006.01) |
| ***A61N 1/36*** | (2006.01) |
| ***A61B 5/12*** | (2006.01) |
| ***G06F 19/00*** | (2011.01) |

(52) U.S. Cl.
CPC .............. *A61N 1/36032* (2013.01); *A61B 5/12* (2013.01); *G06F 19/34* (2013.01)

(58) Field of Classification Search
USPC .................................................. 607/57
See application file for complete search history.

(56) References Cited

U.S. PATENT DOCUMENTS

2004/0094355 A1 * 5/2004 Goorevich et al. ........... 181/129

* cited by examiner

*Primary Examiner* — Robert N Wieland
(74) *Attorney, Agent, or Firm* — Sunstein Kann Murphy & Timbers LLP

(57) ABSTRACT

A system and method for selecting an appropriate implantable hearing device for a patient with a hearing impairment is disclosed. The system includes an auditory parameter generating module configured to receive electronically generated image data of the patient's auditory structure and to generate at least one auditory parameter based on the image data. The system further includes memory, in communication with the auditory parameter generating module, that is configured to store a listing of one or more implantable hearing devices, and a hearing device determining module, in communication with the auditory parameter generating module and the memory, that is configured to select the implantable hearing device based on the auditory parameter.

15 Claims, 16 Drawing Sheets

SYSTEM AND METHOD FOR ELECTRODE SELECTION AND FREQUENCY MAPPING

CROSS REFERENCE TO RELATED APPLICATIONS

The present application claims the benefit of U.S. Provisional Patent Application No. 61/764,778 filed Feb. 14, 2013, the disclosure of which is incorporated by reference herein in its entirety.

TECHNICAL FIELD

The present invention generally relates to tools used with hearing systems and, more particularly, to systems and methods for selecting an appropriate implantable hearing device for use with the treatment of hearing impairments.

BACKGROUND ART

For many patients with hearing impairments, there are several types of implantable hearing devices, such as middle and inner ear implants, that can restore a sense of partial or full hearing. For example, cochlear implants can restore some sense of hearing by direct electrical stimulation of the neural tissue of the cochlea. The cochlear implant typically includes an electrode having an electrode array which is threaded into the cochlea. The electrode array usually includes multiple electrode contacts on its surface that electrically stimulate auditory nerve tissue with small currents delivered by the contacts distributed along the electrode array. These contacts are typically located toward the end of the electrode and are in electrical communication with an electronics module that produces an electrical stimulation signal for the implanted electrode to stimulate the cochlea. In another example, a conventional hearing aid may be used to provide acoustic stimulation to the auditory system in the form of amplified sound when the impairment is related to the operation of the middle ear. In addition, groups of auditory nerve axons may be stimulated with an electrode placed within the modiolus, or auditory structures in the brain may be stimulated with an electrode placed on or within the structures, for example, on or within the cochlear nucleus.

As with many implantable hearing devices, it is desirable to know the device configuration that would best suit a patient's anatomical and hearing needs before implantation of the hearing device. Currently, a surgeon rather blindly selects the cochlear electrode configuration based on subjective judgment and experience with patients in general, rather than based on objective data of the actual patient's hearing impairment and hearing anatomy. This can sometimes result in the selection of a hearing device that does not fit the patient correctly, is not implanted in the proper location, or is unsuitable in other ways.

SUMMARY OF EMBODIMENTS

In accordance with one embodiment of the invention, a method of selecting, in a computer system, an appropriate implantable hearing device for a patient with a hearing impairment includes receiving electronically generated image data of the patient's auditory structure, generating at least one auditory parameter based on the image data, and determining the appropriate implantable hearing device based on the auditory parameter.

In accordance with another embodiment of the invention, a hearing device selection system for a patient with a hearing impairment includes an auditory parameter generating module configured to receive electronically generated image data of the patient's auditory structure and to generate at least one auditory parameter based on the image data. The system further includes memory, in communication with the auditory parameter generating module, that is configured to store a listing of one or more implantable hearing devices, and a hearing device determining module, in communication with the auditory parameter generating module and the memory, that is configured to select the implantable hearing device based on the auditory parameter.

In some embodiments, the implantable hearing device may include a cochlear implant having an electrode. The electronically generated image data may include CT data or MRI data or any radiographic data. The auditory parameter may be selected from cochlear duct length, frequency mapping of the cochlear duct length and/or basal diameter. The method may further include graphically displaying the at least one auditory parameter. The implantable hearing device may be graphically shown in relation to the auditory parameter. Generating the at least one auditory parameter may include measuring a basal diameter based on the image data. The system may further include an image display configured to graphically display the at least one auditory parameter and the implantable hearing device in relation to the auditory parameter. The system may further include a user interface configured to receive information related to the hearing impairment of the patient. The information may include residual hearing of the patient, type of electrode, cochlear coverage, and/or location of cochleostomy site. The system further provides an option of calculating the cochlear coverage based on the post-operative image and related to the performance of the patients.

Illustrative embodiments of the invention may be implemented as a computer program product having a computer usable medium with computer readable program code thereon. The computer readable code may be read and utilized by a computer system in accordance with conventional processes. The computer readable code also can be used in mobile devices (e.g., phones, tablets, personal digital assistants (PDAs), etc), for example, the computer readable code may run as an application (app) for easy access on the mobile device.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Various embodiments of the present invention provide a system and method for selecting an appropriate implantable hearing device for a patient with a hearing impairment. The system includes a selection system configured to receive electronically generated image data of the patient's auditory structure and to generate at least one auditory parameter based on the image data and configured to determine the appropriate implantable hearing device based on the auditory parameter. The hearing device may include a middle ear and/or inner ear implant. The benefits of embodiments of the present invention are that the surgeon selects the appropriate hearing device based on objective data of the patient's actual hearing impairment and auditory structure, resulting in an improved selection and placement of the hearing device in the patient. Details of illustrative embodiments are discussed below.

Figure 1:
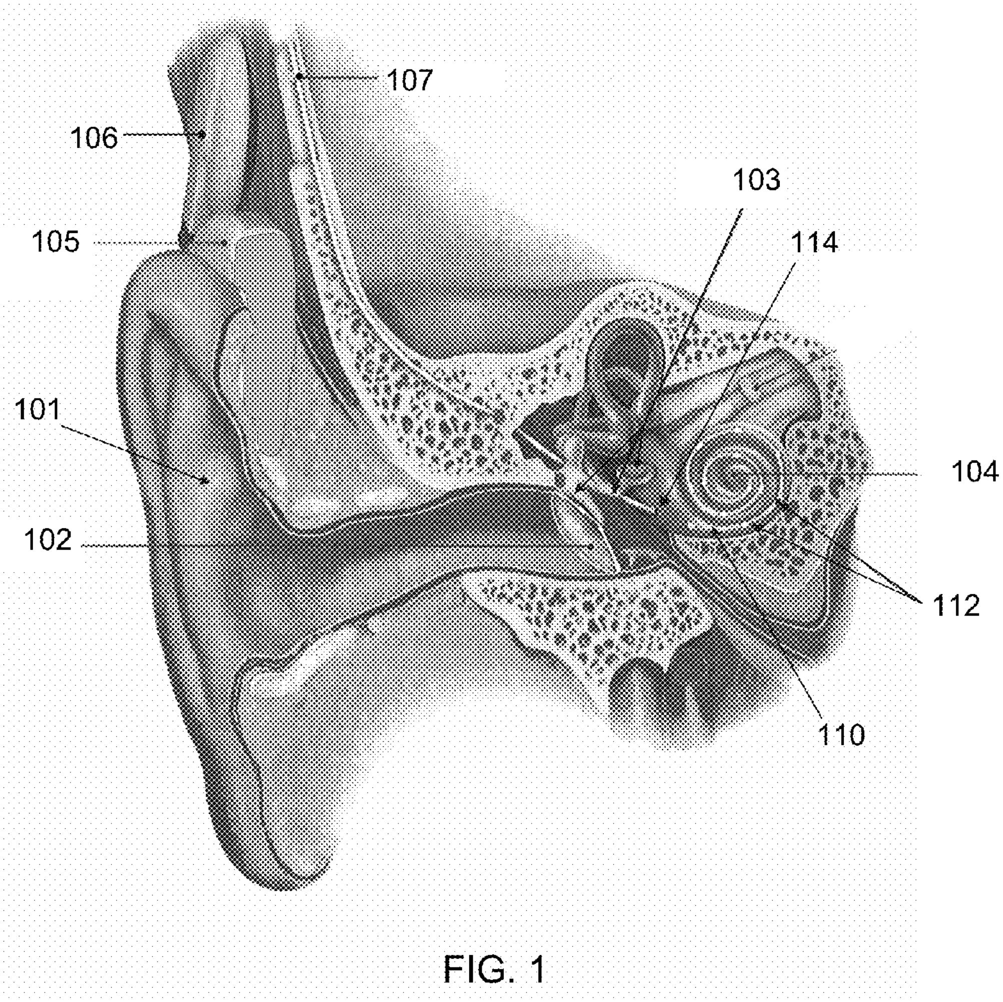
FIG. 1 schematically shows a typical human ear which includes a cochlear implant system.

FIG. 1 schematically shows a portion of the anatomical structure of a normal human ear. The ear typically transmits sounds, such as speech sounds, through the outer ear 101 to the tympanic membrane (eardrum) 102, which moves the bones of the middle ear 103 (malleus, incus, and stapes) that vibrate the oval window membrane of the cochlea 104. The cochlea 104 is a long narrow duct wound spirally about its axis for approximately two and three quarters turns. It includes three chambers along its length, an upper chamber known as the scala vestibuli, a middle chamber known as the scala media, and a lower chamber known as the scala tympani. The cochlea 104 forms an upright spiraling cone with a center called the modiolus where the axons of the auditory nerve reside. These axons project in one direction to the cochlear nucleus in the brainstem and they project in the other direction to the spiral ganglion cells and neural processes peripheral to the cells in the cochlea. In response to received sounds transmitted by the middle ear 103, sensory hair cells in the cochlea 104 function as transducers to convert mechanical motion and energy into electrical discharges in the auditory nerve. These discharges are conveyed to the cochlear nucleus and patterns of induced neural activity in the nucleus are then conveyed to other structures in the brain for further auditory processing and perception.

FIG. 1 also shows some components of a hearing system, such as a typical cochlear implant system, although other hearing systems may be selected using embodiments of the present invention. The cochlear implant system includes an external microphone (not shown) that provides an audio signal input to an external signal processor 105 where various signal processing schemes may be implemented. The processed signal is then converted into a stimulation pattern by an external transmitter/stimulator 106, and the stimulation pattern/signal is transmitted through connected wires (not shown) to an implanted electrode 107. The electrode 107 has an electrode array 110 that is inserted into the cochlea 104 through an opening in the round window or a cochleostomy site 114. Typically, the electrode array 110 has multiple electrode contacts 112 on its surface that provide selective stimulation to the cochlea 104.

Hearing is impaired when there are problems in the ability to transmit sound from the external to the inner ears or problems in the transducer function within the inner ear. To improve impaired hearing, auditory prostheses have been developed. For example, when the impairment is related to the operation of the middle ear 103, a conventional hearing aid may be used to provide acoustic stimulation to the auditory system in the form of amplified sound. When the impairment is associated with the transducer function in the cochlea 104, a cochlear implant system can electrically stimulate auditory neural tissue with small currents delivered by multiple stimulation electrode contacts distributed along at least a part of the cochlear length. Arrays of such stimulation electrode contacts normally are inserted into the scala tympani.

Figure 2:
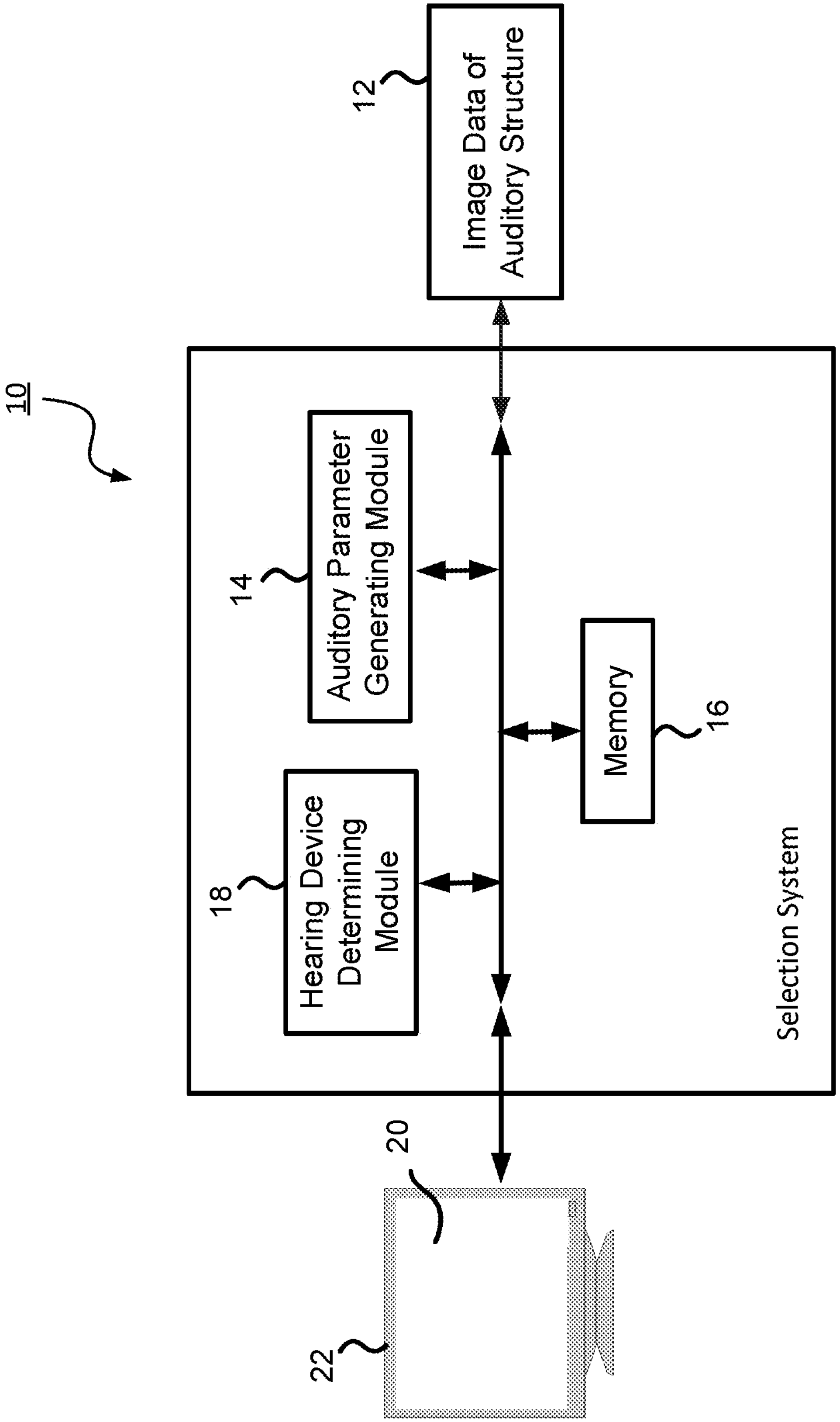
FIG. 2 schematically shows a hearing device selection system according to embodiments of the present invention.
Figure 3:
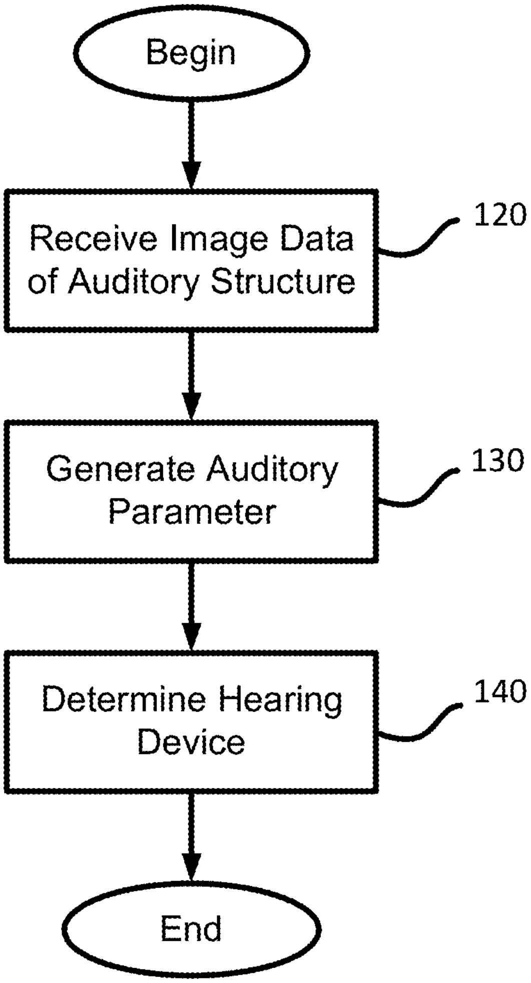
FIG. 3 shows a method of selecting a hearing device for a patient with a hearing impairment according to embodiments of the present invention.

FIG. 2 schematically shows a hearing device selection system 10 and FIG. 3 shows a method of selecting a hearing device for a patient with a hearing impairment according to embodiments of the present invention. Referring to FIGS. 2 and 3, image data 12 of an auditory structure is obtained by known processes. For example, the image data 12 may be electronically generated CT or MRI or any radiographic data of the patient's ear anatomy. The image data 12 of the auditory structure is received (step 120) by an auditory parameter generating module 14 in the selection system 10. The auditory parameter generating module 14 generates one or more auditory parameters (step 130) based on the image data 12. For example, the auditory parameters may include cochlear duct length, frequency mapping of the cochlear duct length, and/or basal diameter.

The basal diameter (the "A" value discussed in more detail below with regard to FIG. 4) may be measured from the CT scan or any radiographic data by drawing a straight line starting from the inside of the round window (RW) opening to the opposite side of the cochlea passing through the helicotrema. This length should be the longest distance from the RW opening to the opposite side of the bony lateral wall of the cochlea. The basal diameter may be manually measured from the image data 12 (e.g., by a surgeon or other person) or may be automatically determined (e.g., by image recognition software).

Based on the basal diameter measurement, the cochlear duct length (CDL) may be determined. The CDL is defined as the length of the cochlear duct measured from the round window entrance up to the helicotrema. It usually includes the 2.5 turns of the cochlea. CDL varies a great deal, regardless of the race, sex and physical size of the patient. Literature shows that the CDL varies from a minimum value of about 25.1 mm to a maximum value of about 36 mm. The length of the cochlear duct measured from the round window entrance up to 2 turns of the cochlea before the helicotrema is reached is designated 2 TL. The 2 TL is important because the maximum electrode insertion cannot be beyond 2 TL due to anatomic constrictions. Therefore, 2 TL is used as one criteria for the electrode selection process in embodiments of the present invention. The summation of Basal Turn Length (BTL) and Middle Turn Length (MTL) accounts for the main portion of the CDL. For example, BTL is about 58% of the CDL, MTL is about 29% of the CDL, and Apical Turn Length (ATL) is about 13% of the CDL.

Another auditory parameter that may be generated is the frequency mapping of the cochlear duct length. The frequency at the Organ of Corti (OC) can be mapped by Greenwood's function as shown below $$F=A*(10^{ax}-k)$$

where F is the frequency in Hz, A is the Greenwood's co-efficient for human=165.4, a=2.1, k=0.88 and finally x as the proportion of total basilar membrane length.

For any cochlear duct length, the end frequencies remain the same (i.e., basal end frequency of 20 kHz and apical end frequency of 20 Hz), but the intermediate frequencies are compressed or distributed depending on the cochlear length, with the critical band distance remaining constant.

The length of the Spiral Ganglion (SG) at Rosenthal's canal is not equal to the length of the Organ of Corti. The SG length is approximately 41.5% of the OC length. The SG extends up to the 2 TL (720'). Therefore, Greenwood's function cannot be used in this case for frequency mapping. Moreover, the critical band distance is not constant as it is with OC length. The nerve fibers that connect the OC to the SG are radial in the basal and the middle regions and the apical 30-40% of OC length is compressed to the apical 20% of the SG length.

Referring again to FIGS. 2 and 3, a listing of one or more appropriate hearing devices may be stored in memory 16 and a hearing device determining module 18, in communication with the auditory parameter generating module 14 and the memory 16, determines the appropriate hearing device(s) (step 140) based on the auditory parameter(s). For example, the listing of hearing devices may be in the form of a database or look-up table with each hearing device having one or more hearing device parameters, such as shown in Table 1.

TABLE 1

| | | RW | | | | Coc | | | |
|---|---|---|---|---|---|---|---|---|---|
| "A" | | 0 | 500 | 750 | 1000 | 0 | 500 | 750 | 1000 |
| 7 | 2TL | F20 | F20 | F20-2 | F20-1C | F20 | F20-2 | F20-1C | F20-2C |
| | 1,5TL | F20-2 | F20-2 | — | — | — | — | — | |
| 7,1 | 2TL | F20 | F20 | F20-2 | F20-1C | F20 | F20-2 | F20-2C | F20-3C |
| | 1,5TL | F20-2 | F20-2 | F20-3 | F20-1C | F20-1C | F20-1C | — | — |
| 7,2 | 2TL | F20 | F20 | F20-2 | F20-3 | F20 | F20-2 | F20-1C | F20-2C |
| | 1,5TL | F20-1 | F20-2 | F20-2 | — | F20-1C | F20-1C | — | — |
| 7,3 | 2TL | F20 | F20 | F20-2 | F20-3 | F20 | F20-2 | F20-1C | F20-2C |
| | 1,5TL | F20-1 | F20-2 | F20-2 | — | F20-1C | F20-1C | — | — |
| 7,4 | 2TL | F24 | F20 | F20-2 | F20-3 | F20 | F20-2 | F20-3 | F20-1C |
| | 1,5TL | F20-1 | F20-1 | F20-2 | — | F20-2 | F20-2 | — | — |
| 7,5 | 2TL | F24 | F20 | F20-2 | F20-3 | F20 | F20-2 | F20-3 | F20-1C |
| | 1,5TL | F20-1 | F20-1 | F20-2 | — | F20-2 | F20-2 | — | — |
| 7,6 | 2TL | F24 | F20 | F20 | F20-2 | F24-2 | F20 | F20-2 | F20-1C |
| | 1,5TL | F20 | F20 | F20 | — | F20 | F20 | F20-2 | — |
| 7,7 | 2TL | F24 | F20 | F20 | F20-2 | F24-2 | F20 | F20-2 | F20-1C |
| | 1,5TL | F20 | F20 | F20 | — | F20 | F20 | F20-2 | — |
| 7,8 | 2TL | F24 | F20 | F20 | F20-2 | F24-2 | F20 | F20-2 | F20-1C |
| | 1,5TL | F20 | F20 | F20 | — | F20-2 | F20-2 | — | — |
| 7,9 | 2TL | F24 | F20 | F20 | F20-2 | F24-2 | F20 | F20-2 | F20-1C |
| | 1,5TL | F20 | F20 | F20 | — | F20-2 | F20-2 | — | — |
| 8 | 2TL | F24 | F20 | F20 | F20-2 | F24 | F20 | F20-1 | F20-2 |
| | 1,5TL | F20 | F20 | F20 | — | F20-1 | F20-1 | — | — |
| 8,1 | 2TL | F28-2; F24 | F20 | F20 | F20-2 | F24 | F20 | F20-1 | F20-2 |
| | 1,5TL | F20 | F20 | F20 | — | F20-1 | F20-1 | — | — |
| 8,2 | 2TL | F28-2; F24 | F24 | F20 | F20-1 | F24 | F20 | F20 | F20-2 |
| | 1,5TL | F24-2 | F20 | F20 | — | F20 | F20 | F20-1 | — |

The hearing device determining module 18 may then compare the one or more auditory parameters with the one or more hearing device parameters to determine the best choice and fit for the patient. The hearing device selection system 10 may include a user interface 20 that may be displayed on a display device 22.

Figure 4:
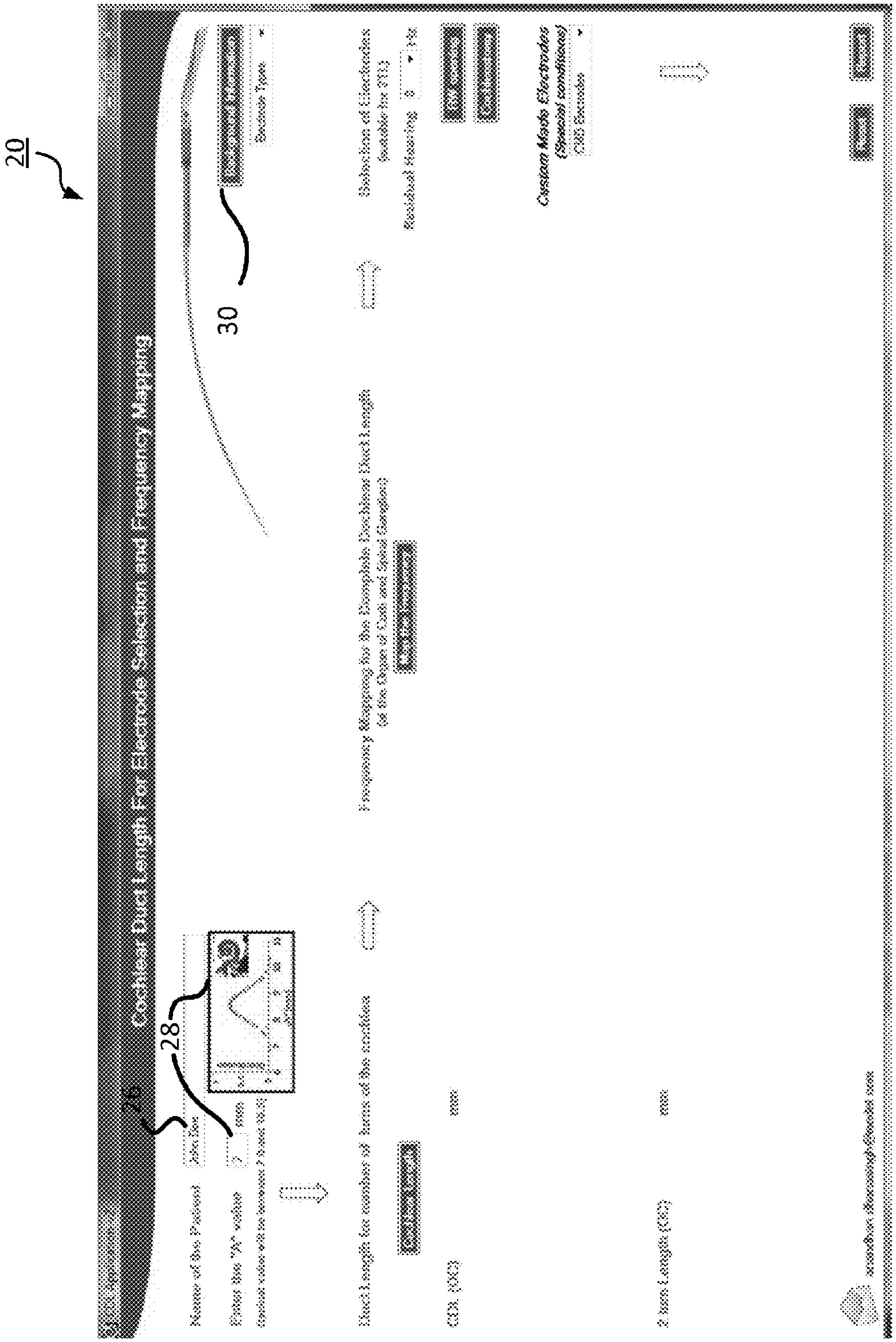
FIG. 4 schematically shows a user interface used in the hearing device selection system according to embodiments of the present invention.

For example, FIG. 4 schematically shows an exemplary user interface 20 that may be used in the hearing device selection system according to embodiments of the present invention. The user interface 20 may include a patient information area 26 for entering and/or displaying information related to the patient, such as the patient's name. The user interface 20 may also include a hearing structure information area 28 for entering and/or displaying hearing structure information related to the patient. For example, the hearing structure information area 28 may show the patient's CT scan (or any radiograph) or the measured "A" value of the patient. The hearing structure information area 28 may also display a typical graph of the "A" value of patients in general to help aid in the "A" value measurement.

Figure 5A:
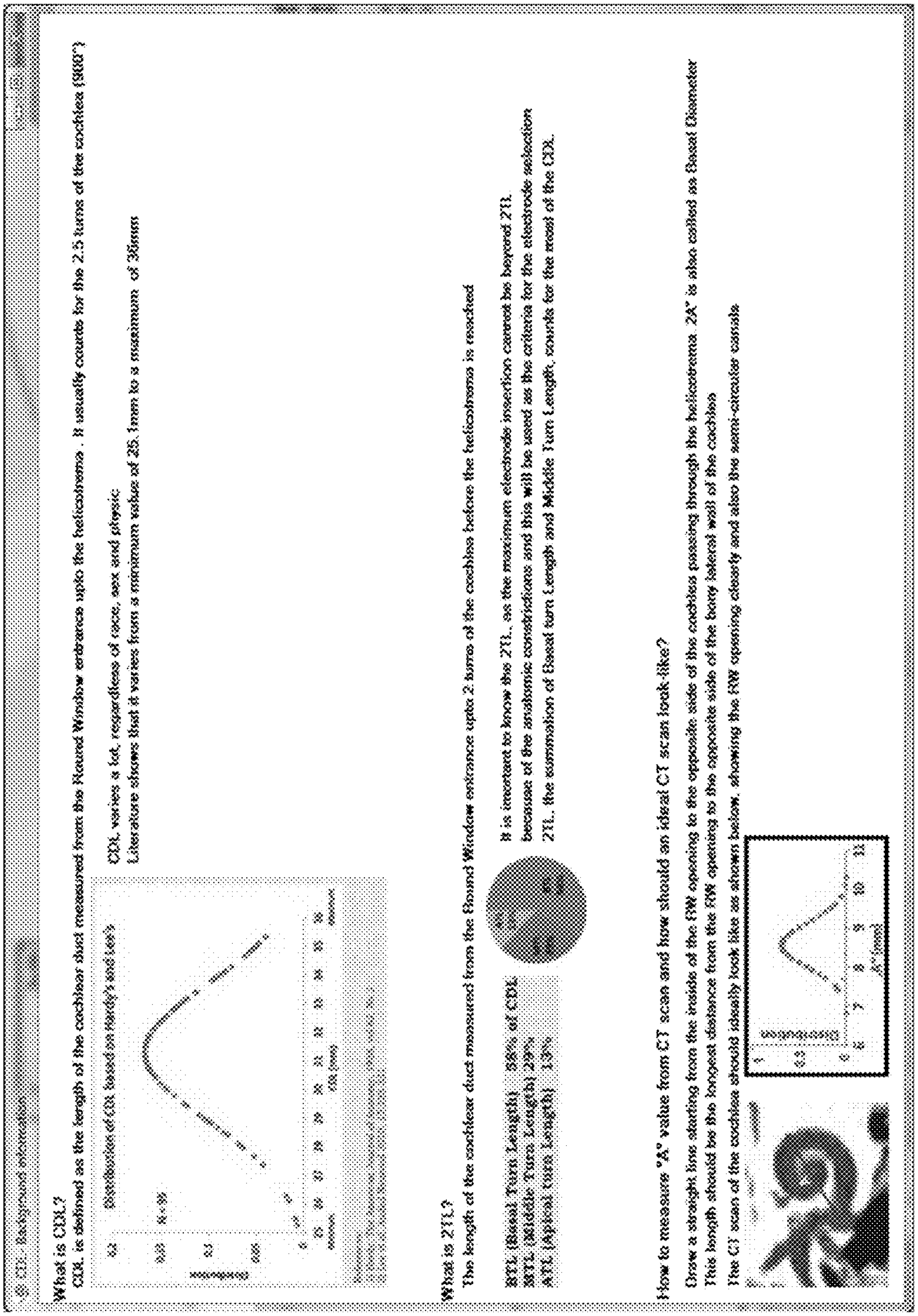
FIGS. 5A-5C schematically show exemplary background information accessed according to embodiments of the present invention.
Figure 5B:
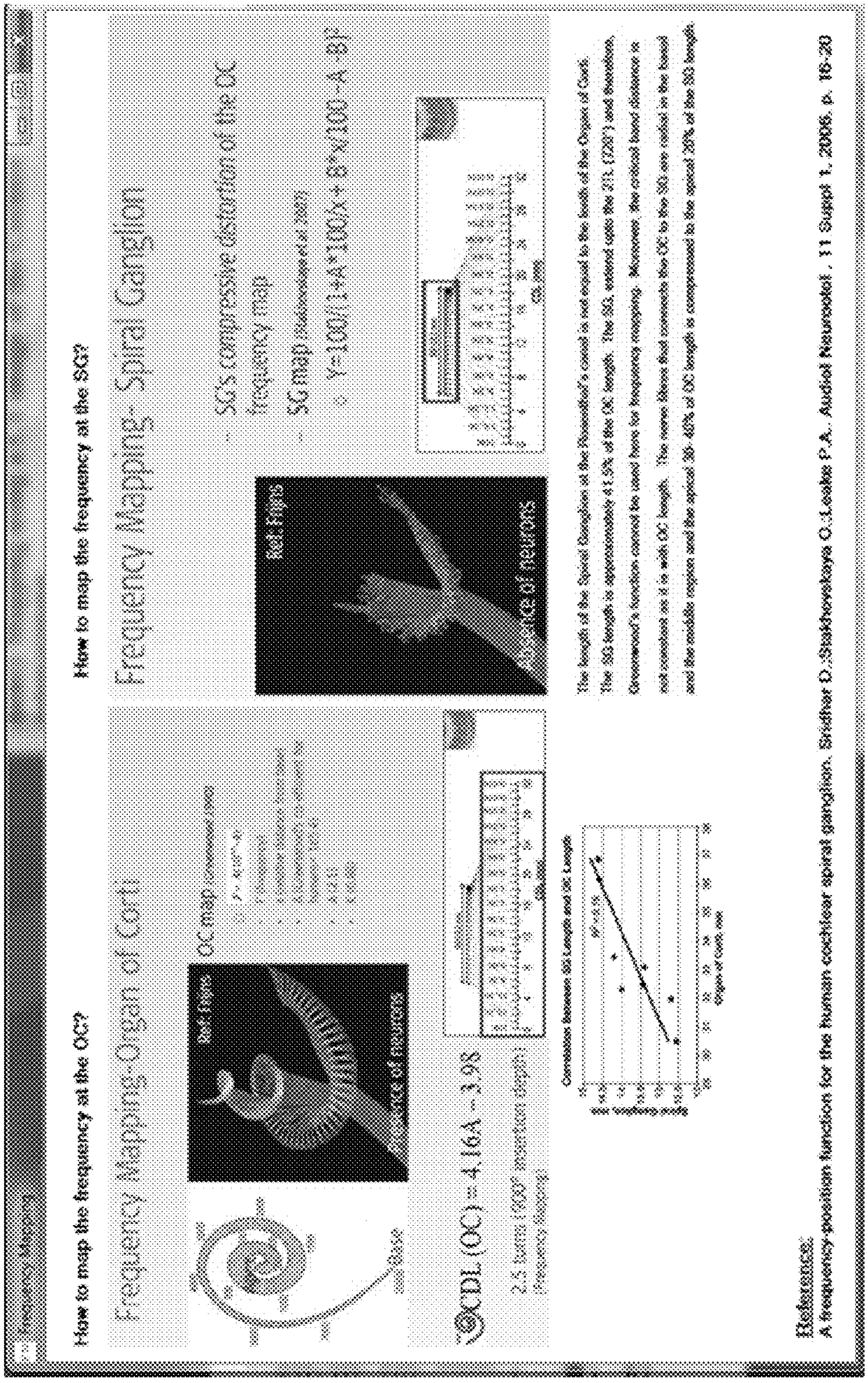
Figure 5C:
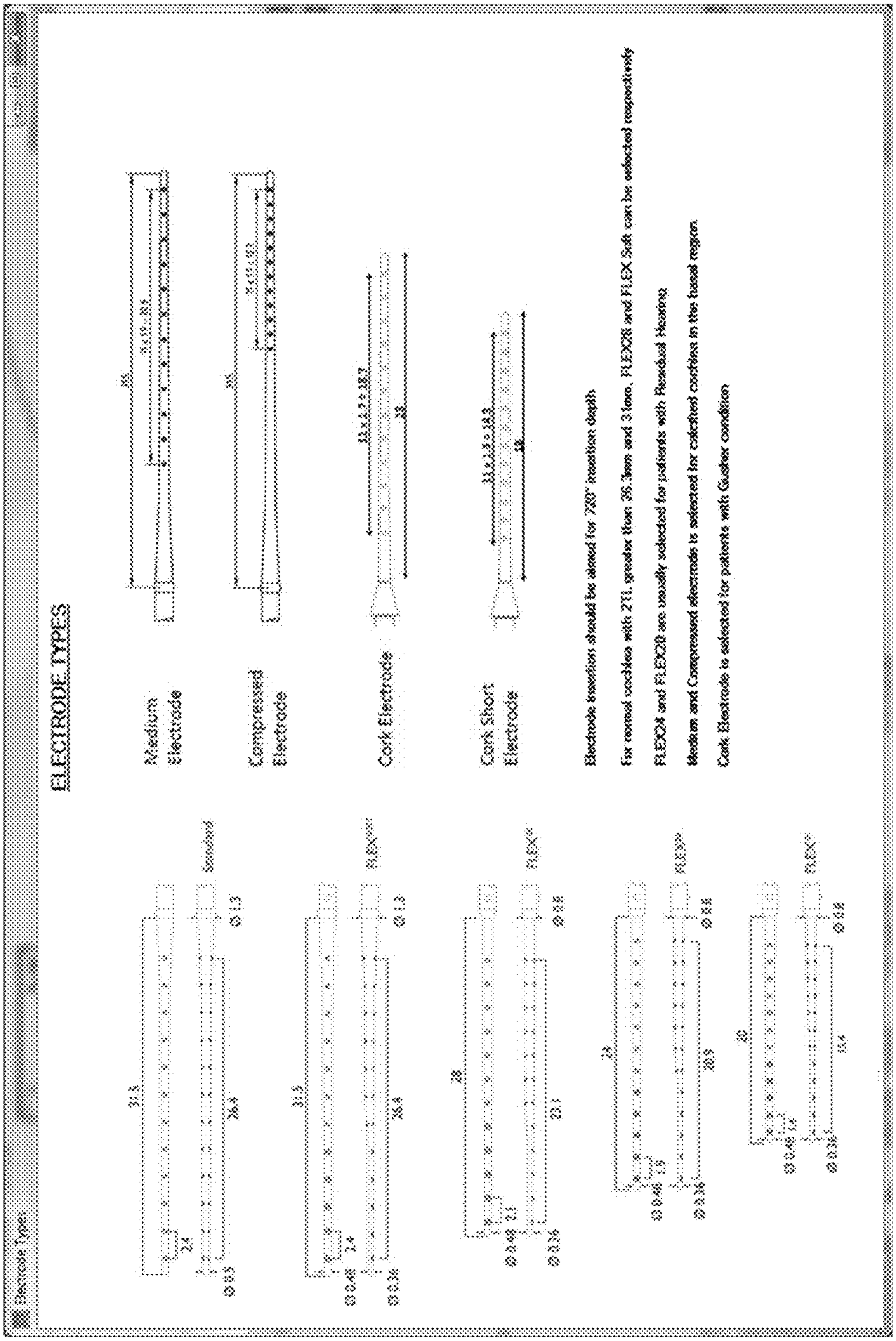

The user interface 20 may also include a background information area 30 where general information about the process may be accessed. For example, FIGS. 5A-5C show some exemplary background information that may be provided, such as an explanation of the CDL or 2 TL, as shown in FIG. 5A. The background information may also provide a typical CT scan or any radiograph showing the RW opening and the semi-circular canals and may include an explanation of how to measure the "A" value from the CT scan, as shown in FIG. 5A. The background information may also include an explanation of how to map the frequency at the OC, how to map the frequency at the SG, or how the nerve fibers connect the OC to the SG, as shown in FIG. 5B. For example, the critical band distance may be graphically shown as it varies with respect to OC, as shown in FIG. 5B. The background information may also provide various types of electrodes that may be selected using embodiments of the present invention, as shown in FIG. 5C.

Figure 6:
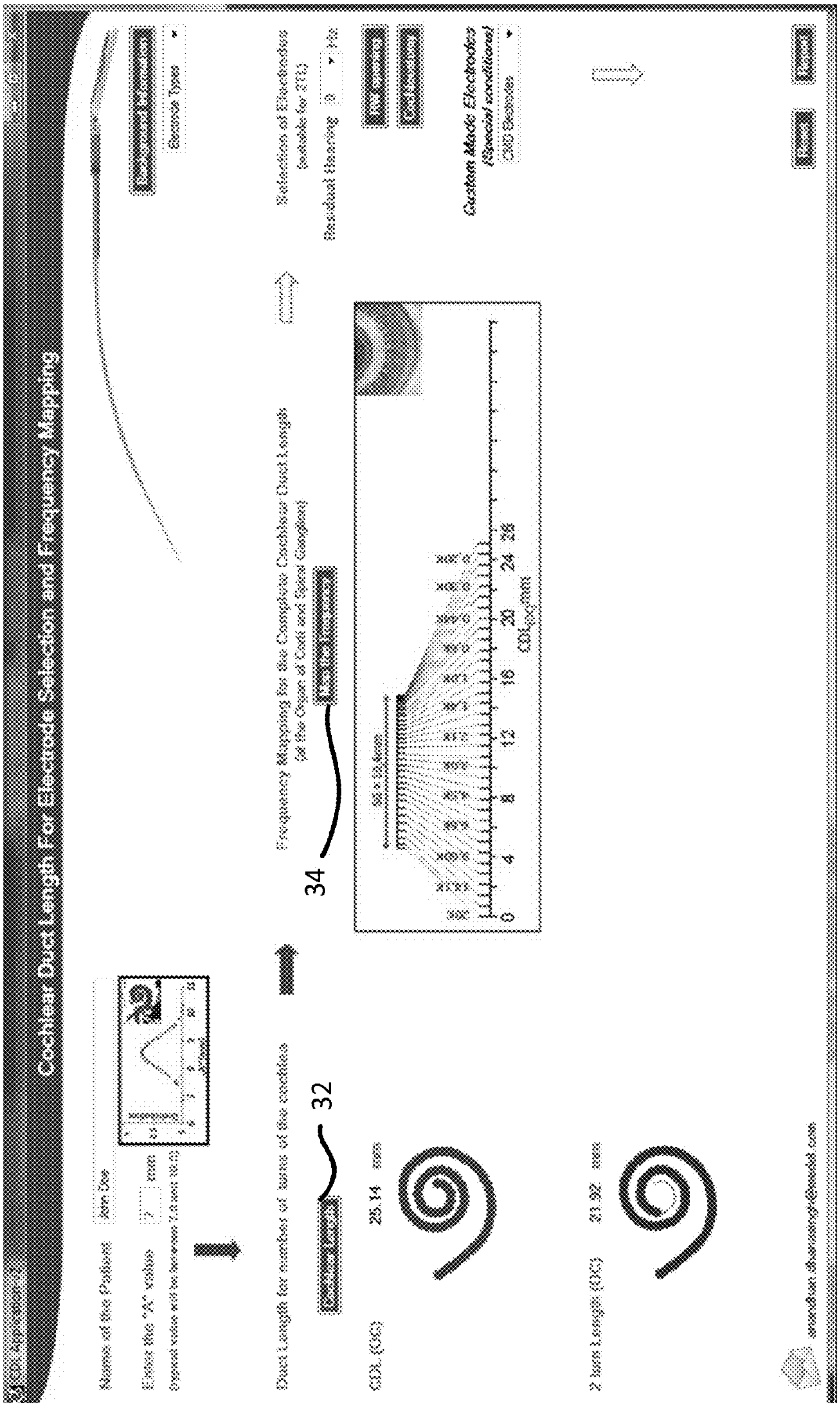
FIG. 6 schematically shows a user interface displaying the duct length and frequency mapping according to embodiments of the present invention.
Figure 7A:
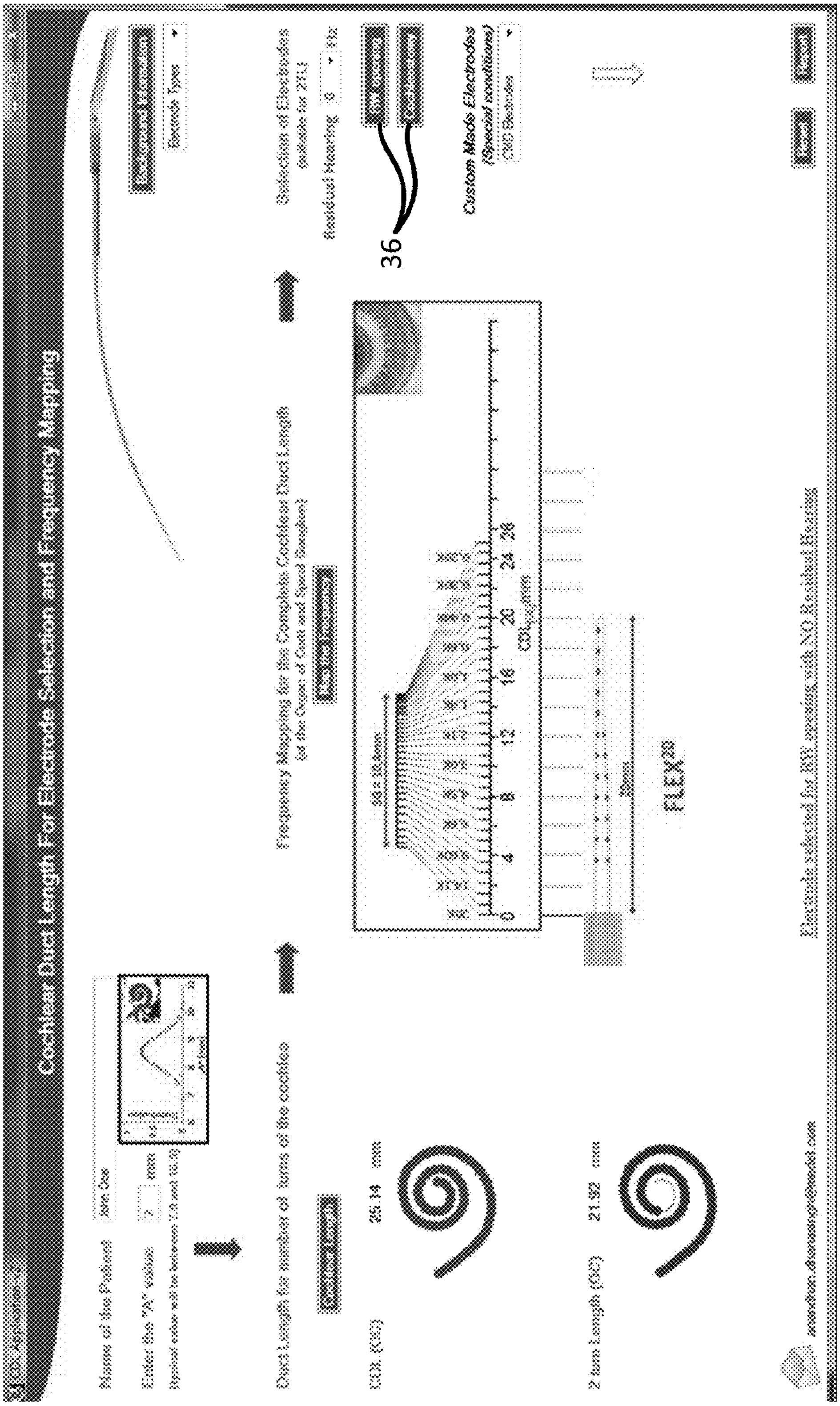
FIGS. 7A-7C schematically show a user interface displaying the frequency mapping and an appropriate hearing device according to embodiments of the present invention.
Figure 7B:
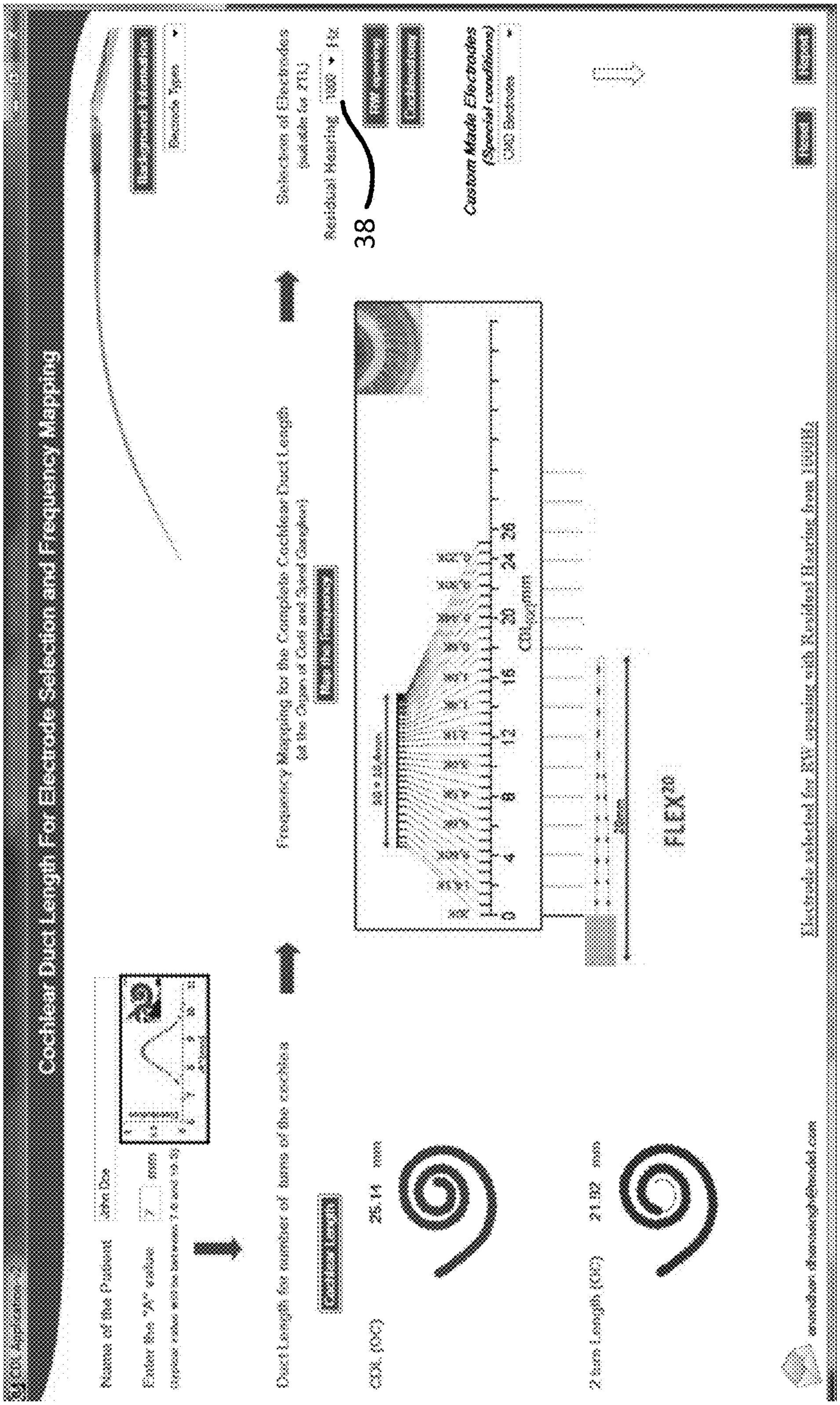
Figure 7C:
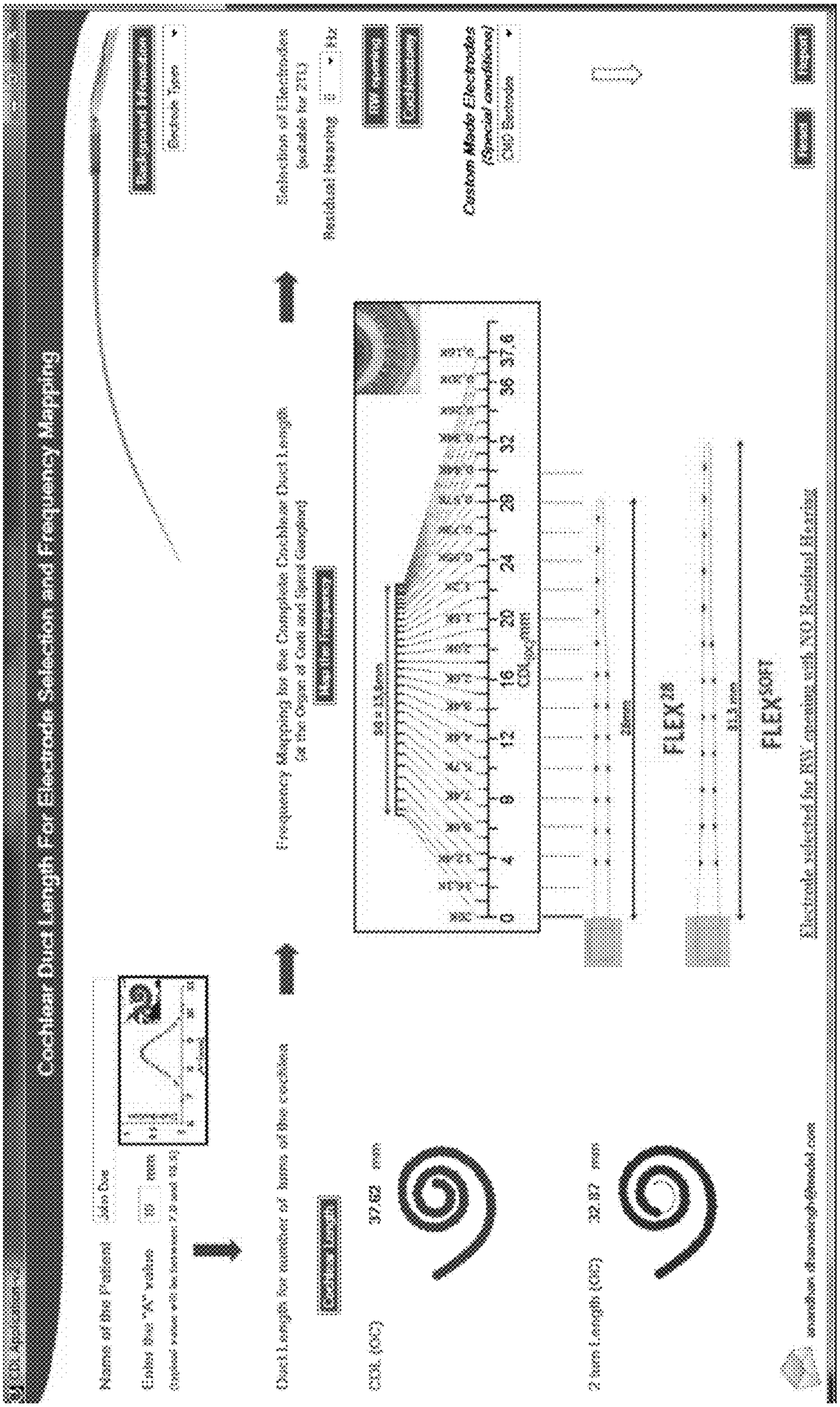

As shown in FIG. 6, the user interface 20 may graphically display a cochlear length 32 (CDL and/or 2 TL) and a frequency mapping 34 for the cochlear duct length based on the auditory parameter(s) of the patient. The selection of the appropriate hearing device may be determined based on the auditory parameter(s), and the user interface 20 may graphically show the appropriate hearing device in relation to one or more of the auditory parameters, such as shown in FIGS. 7A-7C. Information related to the patient's hearing and hearing treatment options may also be entered and/or selected. For example, as shown in FIG. 7A, the user interface 20 may include options of whether the surgical opening is through a RW opening or through another cochleostomy site 36. In addition, as shown in FIG. 7B, the patient's residual hearing 38 may be entered and/or selected. If more than one hearing device is appropriate for the patient, then two or more devices may be graphically shown, as shown in FIG. 7C.

Figure 8:
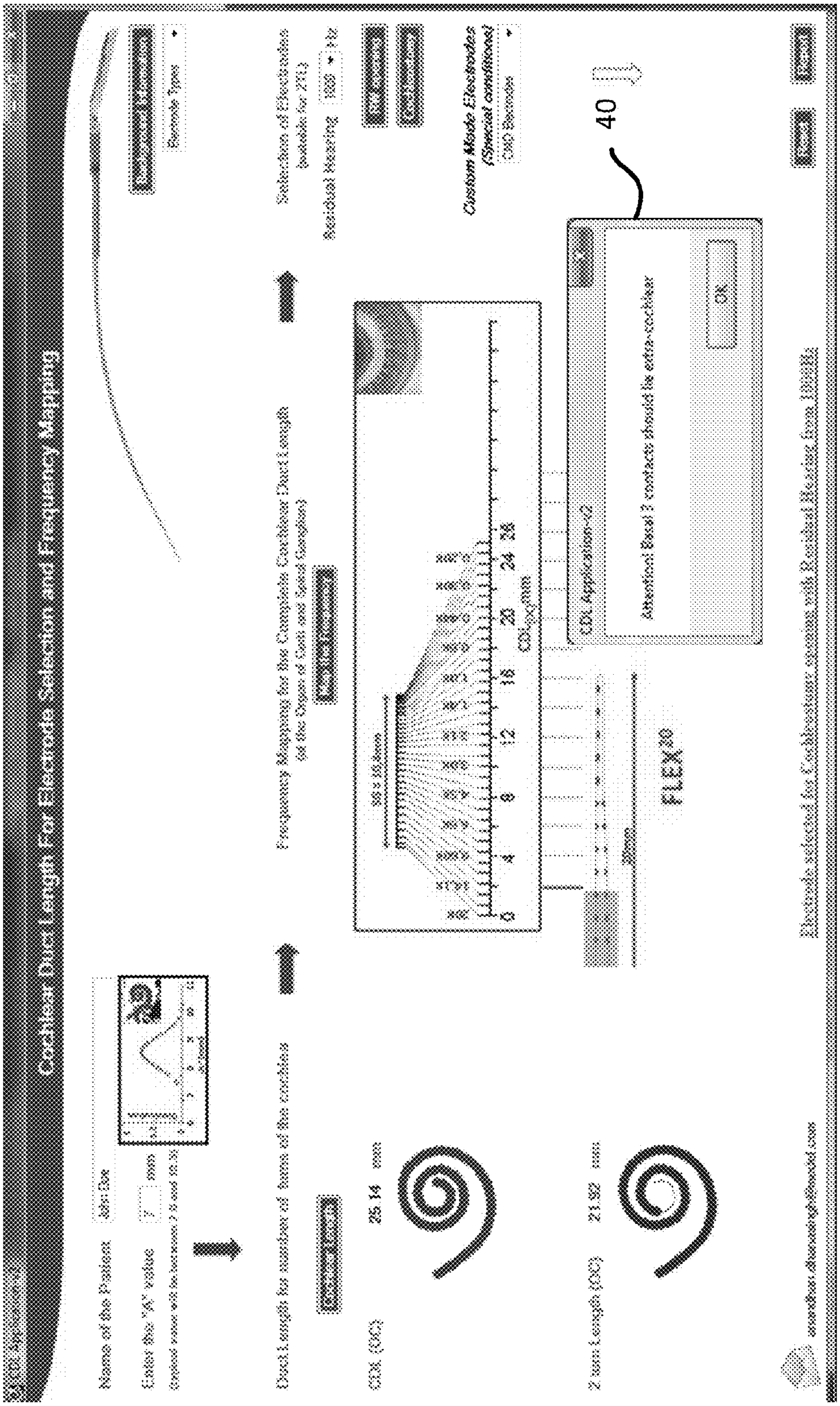
FIG. 8 schematically shows a user interface displaying warnings about an appropriate hearing device according to embodiments of the present invention.
Figure 9:
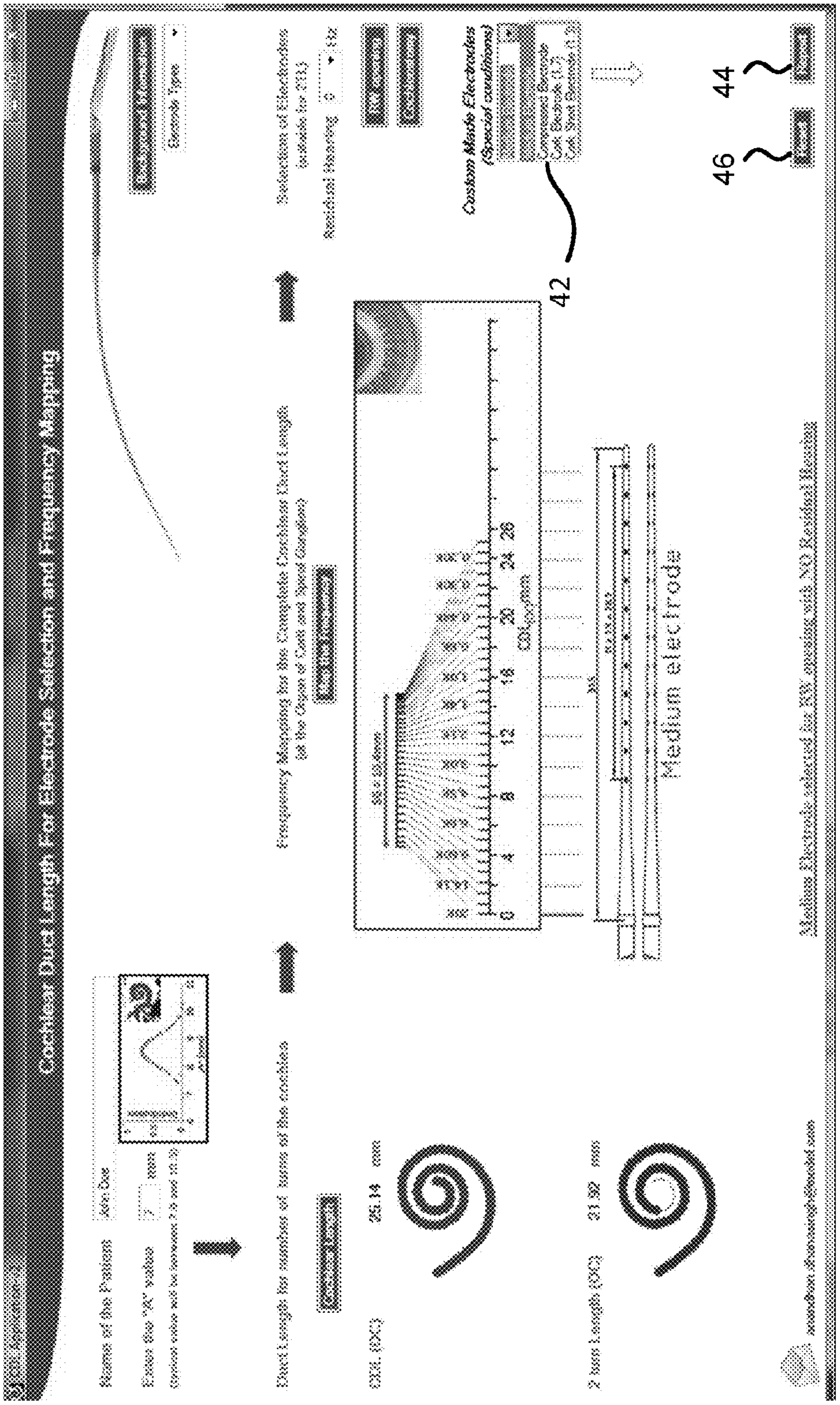
FIG. 9 schematically shows a user interface displaying selection of a custom hearing device according to embodiments of the present invention.
Figure 10:
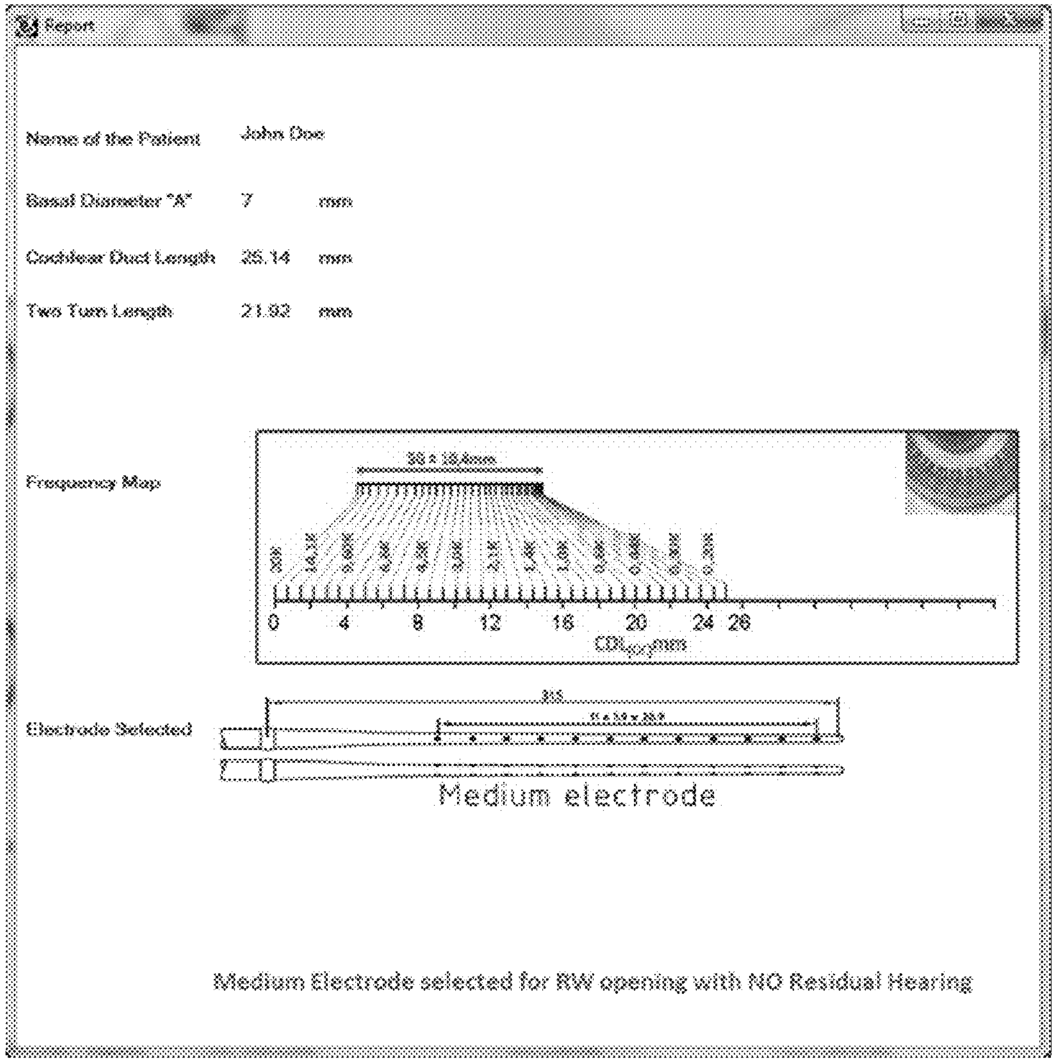
FIG. 10 schematically shows an exemplary report generated according to embodiments of the present invention.

As shown in FIG. 8, the user interface 20 may also provide warnings 40 about the hearing device and its placement. The user interface 20 may also include a custom electrode selection area 42 for entering and/or selecting custom made electrodes for a patient with special circumstances or conditions, such as shown in FIG. 9. The user interface 20 may also allow reports 44 to be generated (such as shown in FIG. 10) or provide the option of resetting 46 the information in the user interface 20, so that the user interface 20 is cleared of the patient information, auditory parameters, and hearing device selection and is ready to accept new patient information (such as shown in FIG. 4).

Figure 11:
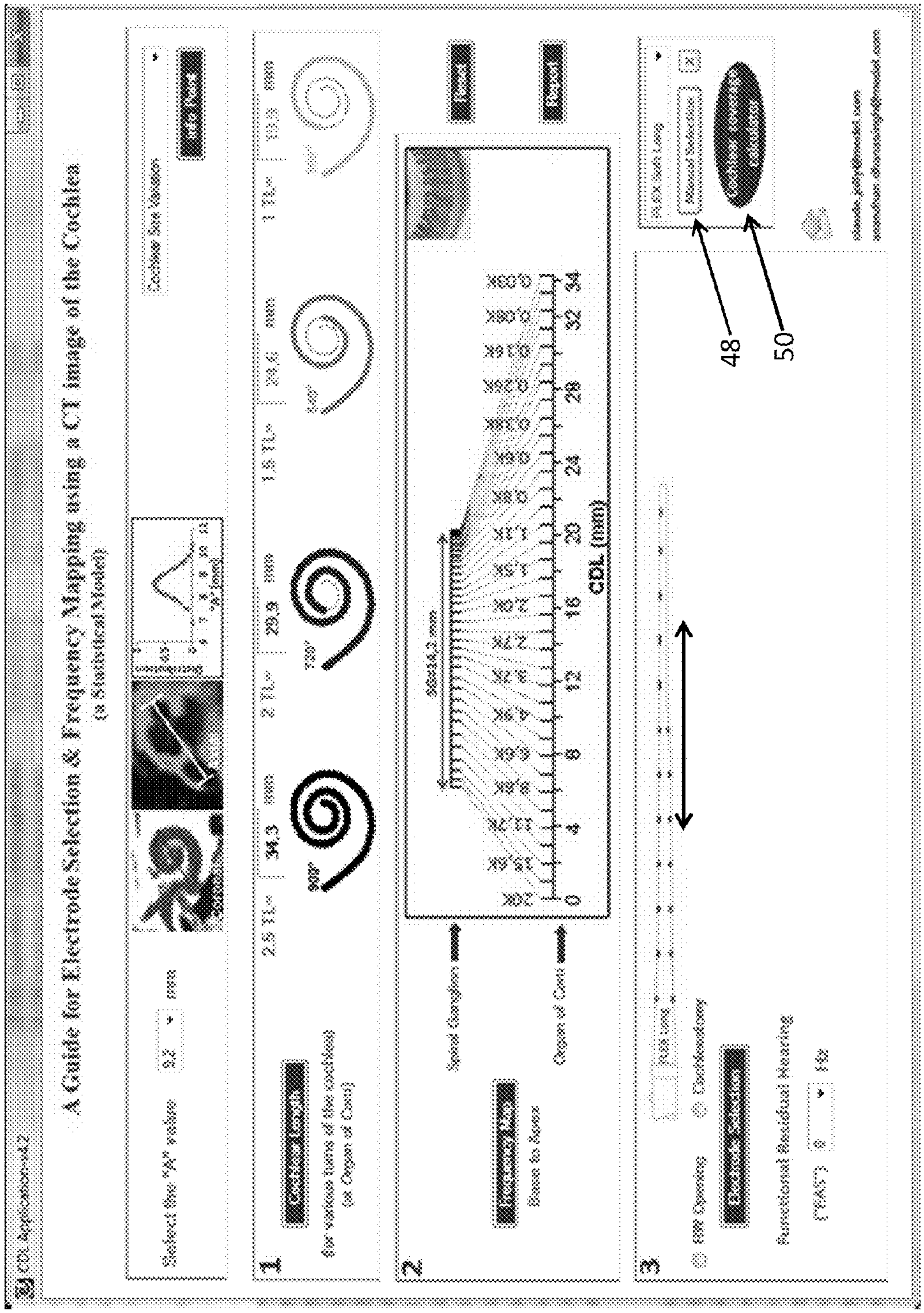
FIG. 11 schematically shows the possibility of selecting any auditory prosthesis manually contrary to the system's proposal according to embodiments of the present invention.

As shown in FIG. 11, the system may also include a manual selection option 48 which the surgeon or an audiologist could use to select the choice of the prosthesis that they want instead of the selection of the system and manually manipulate how good it will fit in for the selected patients.

Although the above discusses the method of using the hearing device selection system 10 to select a hearing device for a patient, the system also may be used when a clinician performs a post-operative fitting by comparing a frequency map, e.g., derived as discussed above with regard to steps 120 and 130, with the position of the electrode, e.g., the electrode contacts. This comparison may assist the clinician in selecting an appropriate frequency allocation of the processed audio signal to the individual contacts.

Figure 12:
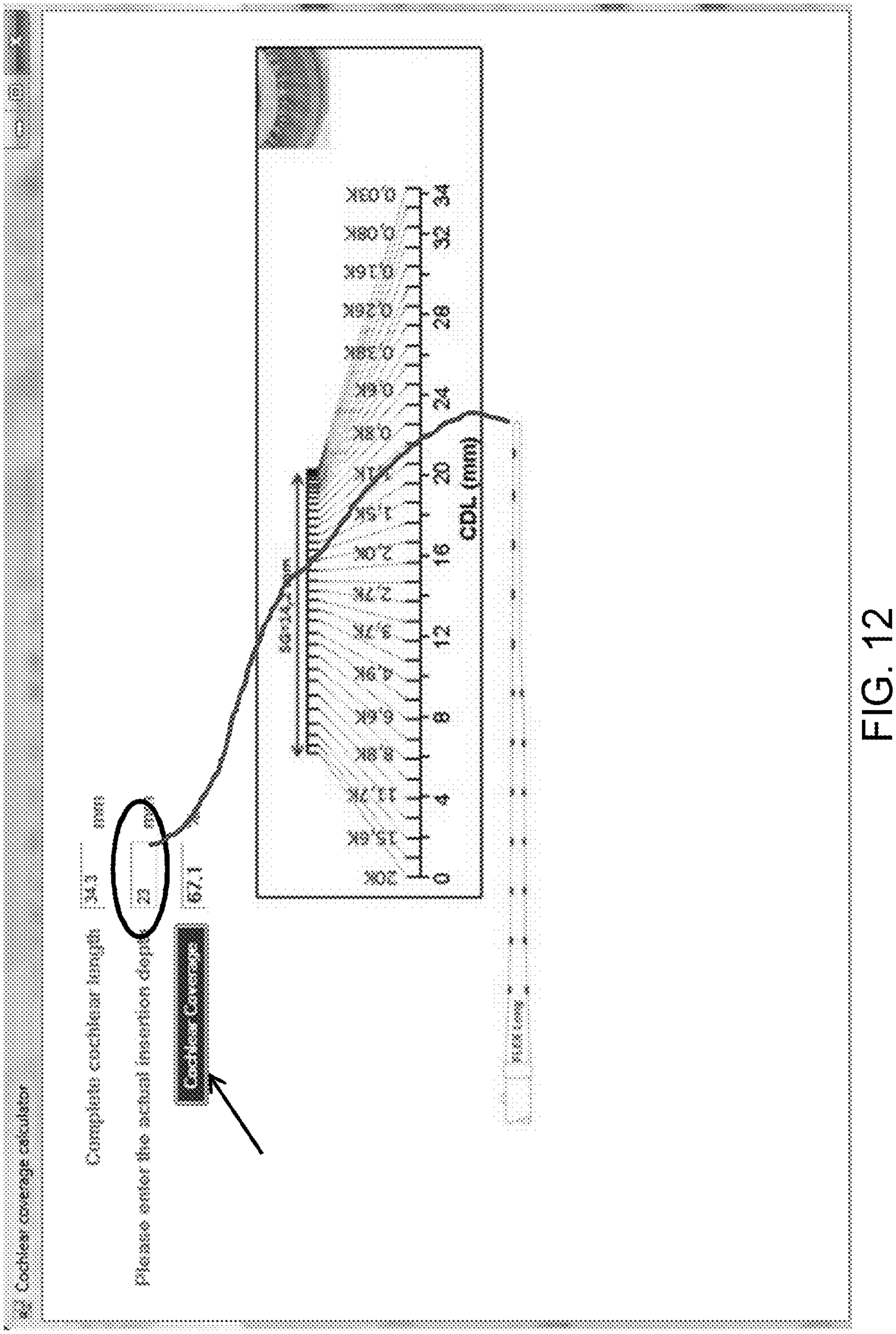
FIG. 12 schematically shows an estimation of the cochlear coverage in percentage and its corresponding insertion depth according to embodiments of the present invention.

As shown in FIGS. 11 and 12, the system may also include an option 50 to estimate the cochlear coverage in percentage and could use that information in estimating the patient performance.

Although a cochlear implant electrode is shown in the user interface 20 and discussed above with regard to the hearing device, other hearing devices may also be used with embodiments of the system and method disclosed herein. For example, a middle ear implant and/or a hearing aid may be used instead of, or in addition to, the cochlear implant.

Among other implementations, the auditory parameter generating module 14 and the hearing device determining module 18 may be a single integrated unit having the discussed functionality, and/or a plurality of interconnected, separate functional devices. Reference to a "module" therefore is for convenience and not intended to limit its implementation. Moreover, the various functionalities within the auditory parameter generating module 14 and the hearing device determining module 18 may be implemented in any number of ways, such as by means of one or more application specific integrated circuits or digital signal processors, or the discussed functionality may be implemented in software.

For example, some embodiments may be implemented as hardware, software (e.g., a computer program product), or a combination of both software and hardware. For instance, embodiments may be implemented as a computer program product for use with a computer system, such as a mobile device (e.g., phone, tablet, personal digital assistant (PDA), etc), and the computer program product may run as an application for easy access on the mobile device. Such implementation may include a series of computer instructions or program code fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the method and system. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although the above discussion discloses various exemplary embodiments of the invention, it should be apparent that those skilled in the art can make various modifications that will achieve some of the advantages of these embodiments without departing from the scope of the invention. For example, although some features may be included in some embodiments and drawings and not in others, these features may be combined with any or all of the other features in accordance with embodiments of the invention as would be readily apparent to those skilled in the art based on the teachings herein.

What is claimed is:

1. A method of selecting, in a computer system, an appropriate implantable hearing device for a patient with a hearing impairment, the method comprising:

receiving electronically generated image data of the patient's auditory structure;

generating at least one auditory parameter based on the image data; and determining the appropriate implantable hearing device based on the auditory parameter.

2. The method of claim 1, wherein the implantable hearing device includes a cochlear implant having an electrode.

3. The method of claim 1, wherein the electronically generated image data includes CT data, MRI data, radiographic data, or combinations thereof.

4. The method of claim 1, wherein the auditory parameter is selected from the group consisting of cochlear duct length, frequency mapping of the cochlear duct length, basal diameter, and combinations thereof.

5. The method of claim 1, further comprising graphically displaying the at least one auditory parameter.

6. The method of claim 5, wherein the implantable hearing device is graphically shown in relation to the auditory parameter.

7. The method of claim 1, wherein generating the at least one auditory parameter includes measuring a basal diameter based on the image data.

8. A hearing device selection system for a patient with a hearing impairment, the system comprising:

an auditory parameter generating module configured to receive electronically generated image data of the patient's auditory structure and to generate at least one auditory parameter based on the image data;

memory, in communication with the auditory parameter generating module, configured to store a listing of one or more implantable hearing devices; and a hearing device determining module, in communication with the auditory parameter generating module and the memory, configured to select the implantable hearing device based on the auditory parameter.

9. The system of claim 8, further comprising an image display configured to graphically display the at least one auditory parameter and the implantable hearing device in relation to the auditory parameter.

10. The system of claim 8, further comprising a user interface configured to receive information related to the hearing impairment of the patient, wherein the information is selected from the group consisting of residual hearing of the patient, type of electrode, location of cochleostomy site, cochlear coverage, and combinations thereof.

11. A computer program product for selecting, in a computer system, an appropriate implantable hearing device for a patient with a hearing impairment, the computer program product comprising a computer usable medium having computer readable program code thereon, the computer readable program code comprising:

program code for receiving electronically generated image data of the patient's auditory structure;

program code for generating at least one auditory parameter based on the image data; and program code for determining the appropriate implantable hearing device based on the auditory parameter.

12. The computer program product of claim 11, wherein the electronically generated image data includes CT data, MRI data, radiographic data, or combinations thereof.

13. The computer program product of claim 11, wherein the auditory parameter is selected from the group consisting of cochlear duct length, frequency mapping of the cochlear duct length, basal diameter, and combinations thereof.

14. The computer program product of claim 11, further comprising:

program code for graphically displaying the at least one auditory parameter.

15. The computer program product of claim 11, wherein the program code for generating the least one auditory parameter includes program code for measuring a basal diameter based on the image data.

* * * * *